United States Patent [19]

Yamazaki et al.

[11] Patent Number: 4,897,261

[45] Date of Patent: Jan. 30, 1990

[54] FINGERNAIL COSMETIC COMPOSITION

[75] Inventors: Kazunori Yamazaki; Muneo Tanaka; Yutaka Okunuki; Yoshikazu Soyama; Masaaki Ishiwatari, all of Yokohama, Japan

[73] Assignee: Shiseido Company Ltd., Tokyo, Japan

[21] Appl. No.: 51,895

[22] Filed: May 19, 1987

[51] Int. Cl.$^4$ .............................................. A61K 7/043
[52] U.S. Cl. ..................................................... 424/61
[58] Field of Search .......................................... 424/61

[56] References Cited

U.S. PATENT DOCUMENTS

| | | | |
|---|---|---|---|
| 2,215,898 | 9/1940 | Anderson | 424/61 |
| 3,257,280 | 6/1966 | Richter | 424/61 |
| 3,335,053 | 8/1967 | Weitzel | 424/61 |
| 3,342,686 | 9/1967 | Jewel et al. | 424/61 |
| 3,441,645 | 4/1969 | Mckissick et al. | 424/61 |
| 3,860,700 | 1/1975 | Viout et al. | 424/61 |
| 4,158,053 | 6/1979 | Greene et al. | 424/61 |
| 4,179,304 | 12/1979 | Rossomando | 424/61 X |
| 4,363,796 | 12/1982 | Bouillon et al. | 424/61 |
| 4,402,935 | 9/1983 | Gordon et al. | 424/61 |
| 4,530,828 | 7/1985 | Smith et al. | 424/61 |

FOREIGN PATENT DOCUMENTS

| | | | |
|---|---|---|---|
| 50-13336 | 5/1975 | Japan . | |
| 54-52736 | 4/1979 | Japan . | |
| 54-160753 | 12/1979 | Japan . | |
| 55-83708 | 6/1980 | Japan . | |
| 57-27082 | 6/1982 | Japan . | |
| 237010 | 10/1985 | Japan | 424/61 |
| 111909 | 5/1987 | Japan . | |

*Primary Examiner*—Ellis P. Robinson
*Assistant Examiner*—Susan S. Rucker
*Attorney, Agent, or Firm*—Sprung, Horn, Kramer & Woods

[57] ABSTRACT

A fingernail cosmetic composition containing at least one resin and at least one organic solvent, characterized by incorporating therein water and a water-incorporating compound having at least one hydrophilic moiety and at least one lipophilic moiety, and, if desired, a moisturizing agent and a fragrance-maintaining agent.

6 Claims, No Drawings

FINGERNAIL COSMETIC COMPOSITION

BACKGROUND OF THE INVENTION

1. Field of the Invention

The present invention relates to a fingernail cosmetic composition having an improved safety factor against damage to a fingernail. More particularly, the present invention relates to a fingernail cosmetic composition which has a high safety factor against damage to a fingernail and does not cause a so-called "split-nail" phenomenon (a peeling of an outermost layer of a fingernail at the tip thereof due to continuous application), while maintaining a stability against separation, an ease of application, and a good coating gloss and a good peeling resistance.

2. Description of the Related Art

Recently, properties of solvent-type fingernail cosmetics have been vastly improved, particularly because of improvements to nitrocellulose lacquers. Thus, such fingernail cosmetics have become an indispensable item among make-up cosmetics.

Among the properties of fingernail cosmetics, the safety of the fingernail is very important. Hitherto, various techniques have been disclosed with respect to compositions of resins and solvents for improving, in particular, the safety factor against damage to fingernails, among the other properties necessary for fingernail cosmetics, i.e., a stability against separation, an ease of application, and a good coating gloss and a good peeling resistance.

As techniques for the improvement of the safety factor in resins, Japanese Examined Patent Publication (Kokai) No. 50-13336 discloses the incorporation of sucrose acetate isobutyrate instead of sulfonamide resin, which decomposes to liberate formalin which may affect the fingernail; Japanese Unexamined Patent Publication (Kokai) No. 54-151142 discloses the incorporation of sucrose benzoate and sucrose acetate isobutyrate instead of toluenesulfonamide/formaldehyde resin; and, Japanese Examined Patent Publication (Kokoku) No. 57-27082 discloses the incorporation of modified alkyd resin instead of aryl sulfonamide condensate. The fingernail cosmetic compositions disclosed in the above patent publications are solvent-type, and do not contain water as a component.

As techniques for the improvement of the safety factor in solvents, Japanese Unexamined Patent Publication (Kokai) No. 54-160753 discloses a harmless fingernail enamel not containing aromatic hydrocarbons such as toluene, xylene or the like, and Japanese Unexamined Patett Publication (Kokai) No. 55-83708 discloses a harmless fingernail lacquer wherein methylene chloride is used in place of conventional solvents in a conventional fingernail lacquer based on cellulose. The fingernail cosmetics disclosed in such Japanese publications are also solvent-type, and do not contain water as a component.

In general, 7 to 12% of water and 0.1 to 1.0% of lipid are contained in a fingernail, but the tip of the fingernail is relatively dry, because the amount of water supplied from the fingernail matrix is lower at the tip than at the central part of the body of the fingernail. Therefore, chipping, breaking, and split-nail phenomena are liable to occur at the tip of the fingernail due to the insufficiency of water thereat.

The conventional solvent-type fingernail cosmetics do not contain water, and thus are unable to supply water to the tip of the fingernail when applied thereon. Further, due to the dehydration action of the solvent, these fingernail cosmetics worsen the split-nail and other phenomena, when continuously applied. Accordingly, these fingernail cosmetics have a disadvantage in that the safety factor against damage to the fingernail is not sufficiently high.

There following may be mentioned as techniques for fingernail cosmetics not containing solvents. Namely, Japanese Unexamined Patent Publication (Kokai) No. 54-28836 discloses a fingernail coating agent comprising an aqueous polymer emulsion prepared by an aqueous emulsion copolymerization of specific monomers, and Japanese Examined Patent Publication (Kokoku) No. 55-43445 discloses an aqueous fingernail cosmetic composition containing a polymer emulsion as a base material. These aqueous fingernail cosmetics have a disadvantage in that, when applied, they have a cold touch and thus can give an unpleasant stimulus, particularly to a person having thin fingernails, because such cosmetics contain a large quantity of water and have high vaporization heat and specific heat values in comparison with organic solvents. These aqueous fingernail cosmetic compositions have another disadvantage in that the water-resistance and adherence to a nail thereof inferior to those of the solvent-type compositions, and thus the peeling resistance is unsatisfactory.

SUMMARY OF THE INVENTION

It has now been found that the above disadvantages can be remedied by incorporating water together with a specific compound into the conventional solvent-type fingernail cosmetic composition.

Accordingly, an object of the present invention is to provide a fingernail cosmetic composition having an improved safety factor against damage to a fingernail and not causing the split-nail phenomenon even with continuous application, while maintaining the various requirements for a fingernail cosmetic composition, i.e., a stability against separation, ease of application, and good coating gloss, good peeling resistance.

Another object of the present invention is to provide a fingernail cosmetic composition having a safety factor superior to that of the above composition of the present invention.

Still another object of the present invention is to provide a fingernail cosmetic composition having an improved stability of fragrance.

Other objects and advantages of the present invention will be apparent from the following description.

In accordance with the present invention, there is provided a fingernail cosmetic composition containing at least one resin and at least one organic solvent, characterized by incorporating therein water and a water-incorporating compound having at least one hydrophilic moiety and at least one lipophilic moiety, and optionally, a moisturizing agent and a fragrance-maintaining agent.

DESCRIPTION OF THE PREFERRED EMBODIMENTS

The term "fingernail cosmetics" used herein means make-up cosmetics applied to a fingernail or toenail for protection and/or beautification thereof. The fingernail cosmetics of the present invention are, in particular, a fingernail enamel, fingernail enamel base coat, or the like.

The conventional fingernail cosmetic composition contains resins and organic solvents as main components. These compositions are, for example, those based on nitrocellulose. The present invention can be applied to any conventional solvent-type fingernail cosmetic compositions, such as those listed above.

The water-incorporating compound used in the present invention is a compound having at least one hydrophilic moiety and at least one lipophilic moiety in the molecule thereof, and capable of incorporating water in the composition.

The term "hydrophilic moiety" means an atom group having a polarity, and thus exhibiting a strong interaction with water. As examples of the hydrophilic moiety, there may be mentioned, a radical of carboxylic acid or carboxylate, sulfonic acid or sulfonate, sulfuric acid or sulfate, phosphoric acid or phosphate, or amine or salt thereof; or hydroxyl, ethylene oxide, nitrile, carbonyl, amide, nitro, imide, or mercapto group; or a moiety of ether bond.

The term "lipophilic moiety" means an atom group showing a nonpolarity and having an extremely weak affinity for water, but a strong affinity for oil. Examples of the lipophilic moiety are a radical of linear or branched, saturated or unsaturated aliphatic hydrocarbon group, saturated or unsaturated alicyclic group, aromatic hydrocarbon, fluorine carbide, or organosilicone compound, and the like.

In the fingernail cosmetic composition of the present invention, water and the water-incorporating compound are incorporated as an internal phase of a water-in-oil emulsion. More particularly, the resins and organic solvents form a continuous external phase of an oil phase, and an aqueous phase is dispersed therein as the internal phase in the form of small particles.

An amount of water incorporated ranges from 0.5 to 30% by weight, preferably 1 to 25% by weight, more preferably 3 to 15% by weight, relative to the total weight of the composition. A composition containing less than 0.5% by weight of water does not show a sufficient improvement of the safety factor for the fingernail, particularly the inhibition of the split-nail phenomenon. A composition containing more than 30% by weight of water is not desirable because, when applied, such a composition gives a strong cold touch and thus an unpleasant stimulus, particularly to a person having thin finger nails.

A weight ratio of the above water-incorporating compound to water is 0.1-200:100, preferably 0.3-50:100, more preferably 0.5-20:100. If the weight ratio of the water-incorporating compound to water is less than 0.1%, the stability against separation of water-in-oil emulsion is degraded. When the above weight ratio is more than 200%, the gloss of the coating and the peeling resistance (resistance to water) thereof are degraded.

The water-incorporating compound which may be used in the present invention is, for example, a water-soluble polymer, an oil-soluble polymer, or a surface-active agent.

The term "water-soluble polymer" used herein means the compound having an average molecular weight of 1,000 to 2,000,000, preferably 2,000 to 1,000,000. The water-soluble polymers which may be used in the present invention are, for example, the water-soluble polymers of celluloses, acrylics, vinyls, polyamides, proteins or polysaccharides. Such polymers can be used alone or in combination.

As examples of the water-soluble cellulosic polymers, there may be cited hydroxyethyl cellulose (e.g., NATROSOL ® 250LR, Hercules), hydroxypropylmethyl cellulose (e.g., METOLOSE ® TC-5, Shin-Etsu Chemical). The water-soluble acrylic polymers are, for example, methacrylate amphoteric polymer (e.g., YUKA-FORMER ® AM-75W, WH, Mitsubishi Petrochemical), poly(sodium acrylate) (e.g., ALON ® A-20P, Toagosei Chemical). The water-soluble vinyl polymers are for example, polyvinyl alcohol (e.g., PVA EG-05 ®, Nippon Synthetic Chemical Industry), copolymer of methyl vinyl ether/maleic anhydride (e.g., GANTREZ ® AN-119, General Aniline).

The water-soluble polyamide polymers are, for example α-(N-dimethylamino)-ε-caprolactam-ε-caprolactam-copolymerized-modified nylon (e.g., AQ-Nylon ®, Toray). The water-soluble protein polymers are, for example, sodium caseinate, or gelatin. The water-soluble polysaccharides are, for example, hyaluronic acid or salt thereof, sodium condroitin sulfate, or pullulan.

An amount of the water-soluble polymer used ranges from 0.1 to 200% by weight, preferably 0.5-15% by weight, relative to the weight of the water.

The term "oil-soluble polymer" used herein means the compound having an average molecule weight of 1,000 to 1,000,000, preferably 2,000 to 500,000. The oil-soluble polymers which may be used in the present invention are, for example, the oil-soluble polymers of celluloses, acrylics, amino acids, or proteins. Such polymers can be used alone or in combination.

As examples of the oil-soluble cellulosic polymers, there may be cited ethylhydroxyethyl cellulose (e.g., EHEC-LOW ®, Hercules), dimethylditallow ammonium cellulose sulfate (e.g., Soloid; KELCO), ethyl cellulose (e.g., Ethyl Cellulose N-7 ®, Hercules), nitrocellulose (e.g., Nitrocellulose SS ½, Hercules). The oil-soluble acrylic polymers are, for example, methacrylate ester amphoteric polymer (e.g., YUKAFORMER ® AM-75, Mitsubishi Petrochemical), polyacrylonitrile. The oil-soluble amino acid polymers are, for example, poly (LD-alanine). The oil-soluble protein polymers are, for example, hydrolyzed collagen (e.g., PROMOIS A, Seiwa Kasei). The other oil-soluble polymers are, for example, dextrin fatty ester (e.g., RHEOPEAL KL, Iwase-Kenjiro Shoten).

An amount of the oil-soluble polymer used ranges from 0.1-200% by weight, preferably 0.5-100% by weight, relative to the weight of the water.

The surface-active agents which may be used in the present invention are nonionic, anionic, cationic, and amphoteric surface-active agents. Such agents can be used alone or in combination.

As examples of lipophilic nonionic surface-active agents, there are cited sorbitan fatty acid ester such as sorbitan monooleate, sorbitan monoisostearate, sorbitan monolaurate, sorbitan monopalmitate, sorbitan monostearate, sorbitan sesquioleate, sorbitan trioleate, penta-2-ethyl hexylic acid diglycerol sorbitan, or tetra-2-ethyl hexylic acid diglycerol sorbitan; glycerol polyglycerol fatty acids such as glycerol monocottonseed oil fatty acid, glycerol monoerucate, glycerol sesquioleate, glycerol monostearate, glycerol α,α'-oleate pyroglutamate, or glycerol monostearate malate; propylene glycol fatty acid ester such as propylene glycol monostearate; hardened castor oil derivatives; glycerol alkyl ether or the like.

As examples of hydrophilic nonionic surface-active agents, there may be mentioned polyoxyethylene sorbitan fatty acid ester such as polyoxyethylene sorbitan monooleate polyoxyethylene sorbitan monostearate, or polyoxyethylene sorbitan tetraoleate; polyoxyethylene sorbitol fatty acid ester such as polyoxyethylene sorbitol monolaurate, polyoxyethylene sorbitol monooleate, polyoxyethylene sorbitol pentaoleate, or polyoxyethylene sorbitol monostearate; polyoxyethylene glycerol fatty acid ester such as polyoxyethylene glycerol monostearate, polyoxyethylene glycerol monoisostearate, or polyoxyethylene glycerol triisostearate; polyoxyethylene fatty acid ester such as polyoxyethylene monooleate, polyoxyethylene distearate, polyoxyethylene monodioleate, or ethylene glycol distearate; polyoxyethylene alkyl ether such as polyoxyethylene lauryl ether, polyoxyethylene oleyl ether, polyoxyethylene stearyl ether, polyoxyethylene behenyl ether, polyoxyethylene 2-octyl dodecyl ether, or polyoxyethylene cholestanol ether; polyoxyethylene alkyl phenyl ether such as polyoxyethylene octyl phenyl ether, polyoxyethylene nonyl phenyl ether, or polyoxyethylene dinonyl phenyl ether; pluronic-type surface-active agent such as pluronic; polyoxyethylene polyoxypropylene alkyl ether such as polyoxyethylene polyoxypropylene cetyl ether, polyoxyethylene polyoxypropylene 2-decyl tetradecyl ether, polyoxyethylene polyoxypropylene monobutyl ether, polyoxyethylene polyoxypropylene hydrogenated lanolin, or polyoxyethylene polyoxypropylene glycerol ether; tetrapolyoxyethylene tetrapolyoxypropylene ethylene diamine condensate such as tetronic; polyoxyethylene castor oil or hardened castor oil derivatives such as polyoxyethylene castor oil, polyoxyethylene hardened castor oil monoisostearate, polyoxyethylene hardened castor oil triisostearate, polyoxyethylene hardened castor oil monopyroglutamic acid monoisostearic acid diester, or polyoxyethylene hardened castor oil maleic acid; polyoxyethylene bees wax laurin derivatives such as polyoxyethylene sorbitol bees wax; alkanol amide such as coconut oil fatty acid diethanol amide, lauric acid monoethanol amide, or fatty acid isopropanol amide; polyoxyethylene propylene glycol fatty acid ester, polyoxyethylene alkyl amine, polyoxyethylene fatty acid amide, sucrose fatty acid ester, polyoxyethylene nonyl phenyl formamide condensate, alkyl ethoxy dimethylamine oxide, trioleyl phosphate, or the like.

As examples of anionic surface-active agents, there may be mentioned fatty acid soap such as soap base, sodium laurate or sodium palmitate; a salt of higher alkyl sulfate such as sodium lauryl sulfate or potassium lauryl sulfate; a salt of alkyl ether sulfate such as polyoxyethylene triethanolamine lauryl sulfate, polyoxyethylene sodium lauryl sulfate; N-acyl sarcosinate such as sodium lauroyl sarcosinate; a salt of higher fatty acid amide sulfonic acid such as sodium N-myristoyl-N-methyl taurine, sodium coconut oil fatty acid methyl tauride or sodium lauryl methyl tauride; a salt of phosphate such as polyoxyethylene sodium oleyl ether phosphate, or polyoxyethylene stearyl ether phosphate; a salt of sulfosuccinate such as sodium di-2-ethylhexyl sulfosuccinate, sodium monolauroyl monoethanol amide polyoxyethylene sulfosuccinate, or sodium lauryl polypropylene glycol sulfosuccinate; alkyl benzene sulfonate such as sodium n-dodecyl benzene sulfonate, n-dodecyl benzene sulfonic acid triethanol amine, or n-dodecyl benzene sulfonic acid; a salt of N-acyl glutamate such as monosodium N-lauroyl glutamate, disodium N-stearoyl glutamate, or monosodium N-myristoyl-L-glutamate; a salt of fatty acid ester sulfuric acid ester such as sodium hardened coconut oil fatty acid glycerol sulfate; sulfonated oil such as Turkey red oil; polyoxyethylene alkyl ether carboxylic acid, a salt of polyoxyethylene alkyl aryl ether carboxylic acid, α-olefin sulfonate, higher fatty acid ester sulfonate, a salt of sec-alcohol sulfate, a salt of higher fatty acid alkylol amide sulfate, sodium lauroyl monoethanol amide succinate, N-palmitoyl aspartate ditriethanol amine, or the like.

As examples of cationic surface-active agents, there may be mentioned alkyl trimethyl ammonium salt such as stearyl trimethyl ammonium chloride, or lauryl trimethyl ammonium chloride; alkyl pyridinium salt such as distearyl dimethyl ammonium dialkyl dimethyl ammonium chloride, poly-(N,N'-dimethyl-3,5-methylene piperidinium) chloride, or cetyl pyridinium chloride; alkyl quaternary ammonium salt, alkyl dimethyl benzyl ammonium salt, alkyl isoquinolinium salt, dialkyl morpholinium salt, polyoxyethylene alkylamine, alkylamine salt, polyamine fatty acid derivatives, amylalcohol fatty acid derivatives, benzalkonium chloride, benzethonium chloride, cationic polymer, β-N,N-dimethyl-N-ethyl ammonioethyl acrylate/vinyl pyrrolidone copolymer, or the like.

As examples of amphoteric surface-active agents, there may be mentioned imidazoline amphoteric surfaceactive agent such as sodium 2-undecyl-N,N,N-(hydroxyethylcarboxyethyl)-2-imidazoline, or disodium 2-cocoyl-2-imidazolinium hydroxide-1-carboxyethyloxy; betaine surface-active agent such as 2-heptadecyl-N-carboxymethyl-N-hydroxyethyl imidazolinium betaine, lauryl dimethyl amino acetic acid betaine, alkyl betaine, amide betaine, or sulfobetaine; amino acid salt such as N-lauryl-β-alanine, or N-stearyl-β-alanine, or the like.

An amount of the surface-active agent used ranges from 0.1–200% by weight, preferably 0.2–100% by weight, relative to the weight of the water.

The surface-active agent can be added to the composition of the present invention, after forming a complex with an organo-modified bentonite, which is generally used in order to prevent separation of the pigments incorporated in the composition.

The nitrocellulose, if incorporated in the composition of the present invention, may be any known nitrocellulose conventionally used in such compositions. For example, nitrocelluloses RS types (nitrogen content of 11.5–12.2%) of Hercules, such as nitrocellulose RS ½ second, nitrocellulose RS ¼ second, nitrocellulose RS ⅛ second, nitrocellulose RS 1/16 second or the like can be used. The above nitrocelluloses can be used alone or in combination. The amount of nitrocellulose incorporated ranges from 5–25% by weight (in the form of nitrocellulose having isopropylalcohol wetness of 30%), relative to the total weight of the composition.

The resins used in the present composition may be any known resins conventionally used in such a composition. For example, alkyd resin, acrylic resin, polyester resin, sacrose resin, sulfonamide resin, rosin resin or the like can be used. The above resins can be used alone or in combination. The amount of the resin ranges in general from 10 to 40% by weight, or if nitrocellulose is employed, from 3 to 15% by weight, relative to the total weight of the composition.

The organic solvent used in the present composition may be any known organic solvent conventionally used in such a composition, e.g., esters, alcohols, hydrocarbons, or the like. For example, there may be used ethyl acetate, butyl acetate, amyl acetate, ethyl alcohol, isopropyl alcohol, butyl alcohol, or toluene. The above organic solvents can be used alone or in combination. The amount of the organic solvent used ranges from 30 to 85% by weight, relative to the total weight of the composition.

Into the composition of the present invention, there may be optionally incorporated a plasticizer (e.g., phthalate such as dibutyl phthalate or dioctyl phthalate, citrate such as tributyl citrate, acetyl tributyl citrate or acetyl triethyl citrate, or camphor), pigment, dyestuff, pearling agent, gelling agent based on organo-modified bentonite, drug, ultraviolet light absorber, or the like. It is necessary to ensure that the use of such optional ingredients does not interfere with the achievement of the objects of the present invention.

The fingernail cosmetic composition of the present invention may be prepared by adding, to the conventional fingernail cosmetic composition, water and the water-incorporating compound, separately or simultaneously, or in the form of a mixture thereof, and agitating to effect a homogeneous emulsification.

Further, the stability of the W/O emulsion can be improved by adding powders such as talc, thereby making use of an emulsifying action thereof, or by adding a solution prepared by mixing water in a solvent therefor (e.g., carbitol or dicarbitol).

It has been further found that the fingernail cosmetic composition having a safety factor against damage to a fingernail and an inhibitory effect on the occurrence of a split-nail phenomenon, superior to the above-mentioned composition of the present invention can be obtained, by further adding a moisturizing agent thereto.

The moisturizing agents which may be used in the present invention are, for example, polyol such as glycol (e.g., ethylene glycol, propylene glycol, dipropylene glycol, butylene glycol such as 1,3-butylene glycol, polyethylene glycol), or sugaralcohol (e.g., glycerol, tetritol, pentitol, hexitol or sorbitol), sodium lactate, sodium pyrrolidone carboxylate, or glycerol ethylene oxide adduct. The above moisturizing agent can be used alone or in combination. The amount of moisturizing agent incorporated ranges from 0.1 to 4% by weight, preferably 1 to 3% by weight, relative to the total weight of the composition. If the amount of the moisturizing agent is less than 0.1% by weight, the effect of the addition thereof can not be clearly observed. When the amount is more than 4% by weight, a dry coating obtained therefrom has a weak resistance to water, and thus is easily removable during house work, washing, or shampooing.

The moisturizing agent can be added at any stage of the process for the preparation of the present composition. However, preferably the moisturizing agent is added after dissolved in water.

It has been still further found that the fingernail cosmetic composition will show an improved stability of fragrance and color by further adding a fragrance-maintaining agent.

The fingernail cosmetic composition of the present invention contains water and an organic solvent. Particularly, the present composition based on the nitrocellulose contains as a main solvent an ester such as butyl acetate or ethyl acetate. When such a composition is left to stand at an elevated temperature for an extende period of time, the above ester can be hydrolyzed to liberate a free acid such as an acetic acid. Thus, the fragrance of the composition may be diluted. Such a deleterious change in the fragrance can be prevented by adding the fragrance-maintaining agent in accordance with the present invention.

The term "fragrance-maintaining agent" herein means a compound capable of controlling hydrolyzation of an ester solvent at an elevated temperature. The fragrance-maintaining agents which may be used in the present invention are, for example, a neutral amino acid, a basic amino acid, or a salt of a basic amino acid and an acidic amino acid. The neutral amino acids are, for example, glycine, alanine, valine, serine, cysteine, phenylalanine, proline or the like. The basic amino acids are, for example, lysine, arginine, histidine, or the like. Further, the salts of the amino acids are, for example, salts of arginine-aspartic acid, arginineglutamic acid, lysine-aspartic acid, lysine-glutamic acid, histidine-aspartic acid, or histidine-glutamic acid. The above fragrance-maintaining agents can be used alone or in combination. The amount of fragrance-maintaining agent incorporated ranges from 0.05 to 3% by weight, preferably 0.1 to 1% by weight, relative to the total weight of the composition. If the amount of the fragrance-maintaining agent is less than 0.05% by weight, the effect of the addition thereof can not be clearly observed. When the amount is more than 3% by weight, peeling resistance (resistance to water) thereof is degraded.

The fragrance-maintaining agent can be added at any stage of the process for the preparation of the present composition. However, preferably the moisturizing agent is added after dissolved in water.

The fingernail cosmetic composition of the present invention has an improved safety factor against damage to a fingernail and does not cause the split-nail phenomenon even with continuous application, while maintaining the various requirements for a fingernail cosmetic composition, i.e., a stability against separation, ease of application, coating gloss and removability.

Further, the fingernail cosmetic composition of the present invention containing the moisturizing agent exhibits a higher safety factor against damage to a fingernail and a greater inhibition of the split-nail phenomenon.

Further, the fingernail cosmetic composition of the present invention containing the fragrance-maintaining agent shows an improved stability of fragrance and color.

EXAMPLES

The following examples are intended to illustrate the present invention and in no way limit the scope thereof. In the following examples, all percentages are given as per cent by weight, unless otherwise specified.

EXAMPLES 1 to 9 and COMPARATIVE EXAMPLES 1 to 6

Fifteen kinds of fingernail cosmetic compositions were prepared from the ingredients listed in the following Table 1.

Using the weight ratios shown in the Table 1, acetyltributyl citrate, n-butyl acetate, and toluene were mixed with stirring. To the mixture, nitrocellulose, alkyd resin, sucrose benzoate, and camphor were added and stirred until dissolved. Then, pigment and organo-modified bentonite were added and stirred until dispersed. To the dispersion, an aqueous solution containing a water-soluble polymer solution and, optionally, amino acid and/or dipropylene glycol, was added and stirred until emulsified. Thus, a red-colored fingernail cosmetic composition was formed.

TABLE 1

(% by weight)

| Ingredients | Com. Ex.* 1 | Com. Ex. 2 | Com. Ex. 3 | Ex.** 1 | Ex. 2 | Ex. 3 | Ex. 4 | Ex. 5 | Ex. 6 | Com. Ex. 4 | Com. Ex. 5 | Ex. 7 | Ex. 8 | Ex. 9 | Com. Ex. 6 |
|---|---|---|---|---|---|---|---|---|---|---|---|---|---|---|---|
| 1 Water | — | 0.3 | — | — | — | — | — | — | — | 15 | — | — | — | — | — |
| 2 0.1% hydroxypropylmethyl cellulose aq. soln. (note 1) | — | — | 0.3 | — | — | — | — | — | — | — | — | — | — | — | — |
| 3 0.3% hydroxypropylmethyl cellulose aq. soln. (note 1) | — | — | — | 0.5 | — | — | — | — | — | — | — | — | — | — | — |
| 4 0.5% hydroxypropylmethyl cellulose aq. soln. (note 1) | — | — | — | — | 1 | — | — | — | — | — | — | — | — | — | — |
| 5 1% Na hyaluronate aq. soln. (note 2) | — | — | — | — | — | 5 | — | — | — | — | — | — | — | — | — |
| 6 5% hydroxypropylmethyl cellulose aq. soln. (note 1) | — | — | — | — | — | — | 10 | — | — | — | — | — | — | — | — |
| 7 5% dimethylamino group containing modified nylon aq. soln. (note 3) | — | — | — | — | — | — | — | 15 | — | — | — | — | — | — | — |
| 8 5% methacrylate amphoteric polymer aq. soln. (note 4) | — | — | — | — | — | — | — | — | 15 | — | — | — | — | — | — |
| 9 0.2% hydroxypropylmethyl cellulose aq. soln. (note 1) | — | — | — | — | — | — | — | — | — | — | 15 | — | — | — | — |
| 10 10% hydroxypropylmethyl cellulose aq. soln. (note 1) | — | — | — | — | — | — | — | — | — | — | — | 20 | — | — | — |
| 11 15% dimethylamino group containing modified nylon aq. soln. (note 3) | — | — | — | — | — | — | — | — | — | — | — | — | 25 | — | — |
| 12 20% methacrylate amphoteric polymer aq. soln. (note 4) | — | — | — | — | — | — | — | — | — | — | — | — | — | 30 | — |
| 13 25% methacrylate amphoteric polymer aq. soln. (note 4) | — | — | — | — | — | — | — | — | — | — | — | — | — | — | 35 |
| 14 Salt of arginine-aspartic acid | — | — | — | — | — | — | — | 0.5 | 0.5 | — | — | — | — | — | — |
| 15 Dipropylene glycol | — | — | — | — | — | — | 3 | — | 2 | — | — | — | — | — | — |
| 16 Nitrocellulose RS ¼ (note 5) | 12 | 12 | 12 | 12 | — | 12 | 12 | — | — | — | — | — | — | — | — |
| 17 Nitrocellulose HIG ¼ (note 5) | — | — | — | — | — | — | — | 12 | 12 | 12 | 12 | — | 12 | 12 | 12 |
| 18 Alkyd resin (note 6) | 6 | 6 | 6 | 6 | 6 | 11 | 6 | 6 | 6 | 6 | 6 | 11 | 6 | 6 | 6 |
| 19 Sucrose benzoate | 6 | 6 | 6 | 6 | 18 | 6 | 6 | 6 | 6 | 6 | 6 | 18 | 6 | 6 | 6 |
| 20 Acetyltributyl citrate | 5 | 5 | 5 | 5 | 5 | 5 | 5 | 5 | 5 | 5 | 5 | — | 5 | 5 | 5 |
| 21 Camphor | 3 | 3 | 3 | 3 | 3 | 3 | 3 | 3 | 3 | 3 | 3 | 3 | 3 | 3 | 3 |
| 22 n-Butyl acetate | 51 | 50.7 | 50.7 | 50.5 | 50 | 46 | 38.0 | 35.5 | 33.5 | 36.0 | 36.0 | 31.0 | 26.0 | 21.0 | 16.0 |
| 23 Toluene | 15 | 15 | 15 | 15 | 15 | 15 | 15 | 15 | 15 | 15 | 15 | 15 | 15 | 15 | 15 |
| 24 Pigment (note 7) | 1 | 1 | 1 | 1 | 1 | 1 | 1 | 1 | 1 | 1 | 1 | 1 | 1 | 1 | 1 |
| 25 Organo-modified | 1 | 1 | 1 | 1 | 1 | 1 | 1 | 1 | 1 | 1 | 1 | 1 | 1 | 1 | 1 |

TABLE 1-continued (% by weight)

| Ingredients | Com. Ex.* 1 | Com. Ex. 2 | Com. Ex. 3 | Ex.** 1 | Ex. 2 | Ex. 3 | Ex. 4 | Ex. 5 | Ex. 6 | Com. Ex. 4 | Com. Ex. 5 | Ex. 7 | Ex. 8 | Ex. 9 | Com. Ex. 6 |
|---|---|---|---|---|---|---|---|---|---|---|---|---|---|---|---|
| bentonite | | | | | | | | | | | | | | | |

*Comparative Example
**Example of the present invention
note 1: Hydroxypropylmethyl cellulose is methylcellulose propylene glycol ether (METOLOSE TC-5; Shin-Etsu Chemical)
note 2: Sodium hyaluronate has an average molecular weight of about 1,200,000 (BIOHYALO) 12; Shiseido)
note 3: Dimethylamino group containing modified nylon is a modified nylon formed from copolymerization of α-(N—dimethylamino)-ε-caprolactam and ε-caprolactam (AQ-NYLON; Toray)
note 4: Methacrylate amphoteric polymer is a compound formed by modifying an alkyl methacrylate-N,N—dimethylamino ethyl methacrylate copolymer with monochloroacetic acid amine (YUKAFORMER AM-75W; Mitsubishi Petrochemical)
note 5: Isopropylalcohol wetness of 30%. RS {available from DAICELL, and HIG {available from ASAHI KASEI
note 6: Alkyd resin is a solid alkyd resin (SOLID BEKKOSOL; Japan Reichhold Chemicals)
note 7: Lithol Rubine BCA/titanium dioxide (4/1)

The stability against separation (emulsion), stimulus upon application, coating gloss, removability, and safety factor against damage to a fingernail of the above compositions were evaluated. The test and evaluations procedures were as follows:

Stability against Separation (Stability of emulsion)

Each of samples was charged in two glass bottles (15 ml); one being left to stand at room temperature for 5 months, and the other left to stand at 50° C. for one month. The degree of separation of each was then observed.
The evaluation was carried out as follows:
◎ (good) . . . No separation in either sample
○ (acceptable) . . . Slight separation in one sample or in both
Δ (bad) . . . Separation in one sample or in both
x (unacceptable) . . . considerable separation in one sample or in both Stimulus upon Application (Cool touch)

The sample was charged into a glass bottle with a cap equipped with a brush. Two coats of the sample were then applied to the finger nails of a panel of twenty people. The cool touch was evaluated during a period of 3 minutes after application, and the results were based on the number of the panel members reporting a cold feeling from the sample.

| Evaluation | Number of members reporting receiving cold feeling |
|---|---|
| ◎ (good) | 0–5 |
| ○ (acceptable) | 6–10 |
| Δ (bad) | 11–15 |
| x (unacceptable) | 16–20 |

Ease of Application

The sample was charged into a glass bottle (10 ml) with a cap equipped with a brush. The ease of application was evaluated as follows:

| | |
|---|---|
| ◎ (good) | smooth and easy |
| ○ (acceptable) | smooth |
| Δ (bad) | difficult |
| x (unacceptable) | very difficult |

The sample was uniformly applied on a glass plate using a doctor blade (0.35 mm). After drying at a room temperature for 24 hours, the gloss of the coating was measured using a D-2 glossmeter (Japan Denshoku) at an angle of incidence of 60° and an angle of reflection of 60°. The evaluation was carried out as follows:

| Evaluation | Values measured |
|---|---|
| ◎ (good) | 100 or more |
| ○ (acceptable) | 90 to less than 100 |
| Δ (bad) | 70 to less than 90 |
| x (unacceptable) | less than 70 |

Peeling Resistance (resistance to water)

The sample was uniformly applied on a nylon plate using a doctor blade (0.35 mm). After drying at a room temperature and immersing in water at 25° C. for 2 hours, a cross-cut test (100 sequences 1 mm×1 mm) generally employed in the adhesion evaluation of a paint and vanish was carried out. The evaluation was carried out on the basis of a degree of retention of the sequence of 1 mm×1 mm after the coating had dried.

(good) . . . almost all squares were retained
(acceptable) . . . a few squares were removed
Δ (bad) . . . relatively many squares were removed
x (unacceptable) . . . almost all squares were removed Safety (Split-nail)

A panel of twenty each sample was chosen from among persons who were liable to suffer from split-nails upon continuous application of conventional fingernail enamels. Continuous application (one application per three days) was carried out for 5 months and the evaluation was made on the basis of the number of panel members having split-nail(s), as follows:

| Evaluation | Number of members with split-nail(s) |
|---|---|
| ☆ (excellent) | 0–3 |
| ◎ (good) | 4–5 |
| ○ (acceptable) | 6–10 |
| Δ (bad) | 11–15 |
| x (unacceptable) | 16–20 |

TABLE 2

| Testing Items | Com. Ex. 1 | Com. Ex. 2 | Com. Ex. 3 | Ex. 1 | Ex. 2 | Ex. 3 | Ex. 4 | Ex. 5 | Ex. 6 | Com. Ex. 4 | Com. Ex. 5 | Ex. 7 | Ex. 8 | Ex. 9 | Com. Ex. 6 |
|---|---|---|---|---|---|---|---|---|---|---|---|---|---|---|---|
| Stability against separation | ◎ | x | Δ | O | ◎ | ◎ | ◎ | ◎ | ◎ | x | x | ◎ | ◎ | ◎ | O |
| Stimulus upon application | ◎ | ◎ | ◎ | ◎ | ◎ | ◎ | ◎ | ◎ | ◎ | ◎ | ◎ | O | O | O | Δ |
| Ease of application | ◎ | ◎ | ◎ | ◎ | ◎ | ◎ | ◎ | ◎ | ◎ | ◎ | ◎ | ◎ | ◎ | ◎ | O |
| Gloss of coating | ◎ | ◎ | ◎ | ◎ | ◎ | ◎ | ◎ | ◎ | ◎ | ◎ | ◎ | ◎ | O | O | Δ |
| Peeling resistance (resistance to water) | ◎ | ◎ | ◎ | ◎ | ◎ | ◎ | ◎ | ◎ | ◎ | ◎ | ◎ | ◎ | ◎ | O | Δ |
| Safety (Split-nail) | x | — | x | Δ | O | ◎ | ☆ | ◎ | ☆ | — | — | ◎ | ◎ | ◎ | — |
| Overall evaluation | x | x | Δ | O | O | ◎ | ◎ | ◎ | ◎ | x | x | ◎ | O | O | Δ |

It is apparent from Table 2 that the fingernail cosmetic composition according to the present invention exhibits a good safety factor against damage to fingernails and rarely causes split-nails due to continuous application, and further, has a good stability against separation (emulsification), less stimulus (cold feeling) upon application, an ease of application, a glossy coating, and a good peeling resistance, and thus has satisfactory properties as a fingernail cosmetic composition.

EXAMPLES 10 to 14 and COMPARATIVE EXAMPLES 7 to 9

Eight kinds of fingernail cosmetic compositions were prepared from the ingredients listed in Table 3.

Using the weight ratios shown in the Table 3, acetyltributyl citrate, n-butyl acetate, and toluene were mixed with stirring. To the mixture, nitrocellulose, acrylic resin, sucrose benzoate and camphor were added and stirred until dissolved. Then, pigment and organo-modified bentonite were added and stirred until dispersed. To the dispersion, a solution of oil-soluble polymer (ethylhydroxyethyl cellulose, dimethylditallowammonium cellulose sulfate or dextrin fatty acid ester) in ethanol, and water optionally containing histidine and/or propylene glycol were added and stirred until emulsified. Thus, red-colored fingernail cosmetic compositions were formed.

These nail cosmetic compositions were tested as above-mentioned. The results are listed in Table 4.

TABLE 3

(% by weight)

| Ingredients | Com. Ex. 7 | Com. Ex. 8 | Ex. 10 | Ex. 11 | Ex. 12 | Ex. 13 | Ex. 14 | Com. Ex. 9 |
|---|---|---|---|---|---|---|---|---|
| 1 Water | 20 | 20 | 20 | 20 | 20 | 20 | 1 | 1 |
| 2 Ethylhydroxyethyl cellulose (note 8) | — | 0.01 | 0.05 | 0.5 | — | — | — | — |
| 3 Dimethylditallow ammonium cellulose sulfate (note 9) | — | — | — | — | 0.5 | — | — | — |
| 4 Dextrin fatty acid ester (note 10) | — | — | — | — | — | 0.5 | 0.1 | 3 |
| 5 Histidine | — | — | — | — | 0.3 | 0.3 | — | — |
| 6 Propylene glycol | — | — | — | 2 | — | 2 | — | — |
| 7 Nitrocellulose RS¼ (note 5) | 14 | 14 | 14 | 14 | 14 | 14 | 14 | 14 |
| 8 Acrylic resin (note 11) | 6 | 6 | 6 | 6 | 6 | 6 | 6 | 6 |
| 9 Sucrose benzoate | 6 | 6 | 6 | 6 | 6 | 6 | 6 | 6 |
| 10 Acetyltriethyl citrate | 6 | 6 | 6 | 6 | 6 | 6 | 6 | 6 |
| 11 Camphor | 1.5 | 1.5 | 1.5 | 1.5 | 1.5 | 1.5 | 1.5 | 1.5 |
| 12 n-Butyl acetate | 24.5 | 24.49 | 24.45 | 22.0 | 23.7 | 21.7 | 43.4 | 40.5 |
| 13 Toluene | 15 | 15 | 15 | 15 | 15 | 15 | 15 | 15 |
| 14 Pigment (note 12) | 1 | 1 | 1 | 1 | 1 | 1 | 1 | 1 |
| 15 Organo-modified bentonite | 1 | 1 | 1 | 1 | 1 | 1 | .1 | 1 |
| 16 Ethanol | 5 | 5 | 5 | 5 | 5 | 5 | 5 | 5 | note 8: Mixed cellulose ether wherein many of the three OH groups in cellulose are substituted with ethoxyl or ethylhydroxyl groups, having a viscosity of 20–35 cps (at 25° C.) as 5% solution in toluene/95% ethanol (80:20) (EHEC-LOW ®; Hercules)
note 9: Having a molecular weight of about 1,000,000 and containing 10–20% of sulfuric acid group and 1.5–3% of nitrogen (SOLOID ®; KELCO)
note 10: Average degree of polymerization of dextrin . . . 20; average degree of esterification . . . 2.5; $C_{16}$-fatty acid (RHEOPEARL KL; Iwase-Kenjiro Shoten)
note 11: Copolymer of butyl acrylate and methyl methacrylate (70:30) having a molecular weight of about 2,000 (OLIGEM BM-3; Matsumoto)
note 12: Deepmaroon/titanium dioxide (4/1)
note 4: Same as Table 1

TABLE 4

Fingernail Cosmetic Compositions

| Testing Items | Com. Ex. 7 | Com. Ex. 8 | Ex. 10 | Ex. 11 | Ex. 12 | Ex. 13 | Ex. 14 | Com. Ex. 9 |
|---|---|---|---|---|---|---|---|---|
| Stability against separation | x | Δ | O | ◎ | ◎ | ◎ | ◎ | ◎ |
| Stimulus upon application | ◎ | ◎ | ◎ | ◎ | ◎ | ◎ | ◎ | ◎ |
| Ease of application | ◎ | ◎ | ◎ | ◎ | ◎ | ◎ | ◎ | ◎ |

TABLE 4-continued

| | Fingernail Cosmetic Compositions | | | | | | | |
|---|---|---|---|---|---|---|---|---|
| Testing Items | Com. Ex. 7 | Com. Ex. 8 | Ex. 10 | Ex. 11 | Ex. 12 | Ex. 13 | Ex. 14 | Com. Ex. 9 |
| Gloss of coating | ⊚ | ⊚ | ⊚ | ⊚ | ⊚ | ⊚ | ⊚ | ⊚ |
| Peeling resistance (resistance to water) | ⊚ | ⊚ | ⊚ | ⊚ | ⊚ | ⊚ | ⊚ | x |
| Safety (Split-nail) | — | ⊚ | ⊚ | ☆ | ⊚ | ☆ | ○ | ○ |
| Overall evaluation | x | Δ | ○ | ⊚ | ⊚ | ⊚ | ○ | x |

It is apparent from Table 4 that the fingernail cosmetic composition according to the present invention exhibits a good safety factor against damage to a fingernail and rarely causes split-nails due to continuous application, and further has a good stability against separation (emulsification), less stimulus (cold feeling) upon application, an ease of application, a glossy coating, and a good peeling resistance (resistance to water) and thus has satisfactory properties as a fingernail cosmetic composition.

EXAMPLES 15 to 21 and COMPARATIVE EXAMPLES 10 to 12

Ten kinds of fingernail cosmetic compositions were prepared from the ingredients listed in Table 5.

Using the weight ratios shown in Table 5, acetyltributyl citrate, n-butyl acetate and toluene were mixed with stirring. To the mixture, nitrocellulose, acrylic resin and camphor were added and stirred until dissolved. Then, pigment and organo-modified bentonite were added and stirred until dispersed. To the dispersion, an aqueous solution containing a mixture prepared by adding to water a surface-active agent and, optionally, glycine and/or glycerol and homogeneously stirring was added and stirred until emulsified. Thus, red-colored fingernail cosmetic compositions were formed.

These fingernail cosmetic compositions were tested as above-mentioned. The results are listed in Table 6.

TABLE 5

| | | (% by weight) | | | | | | | | |
|---|---|---|---|---|---|---|---|---|---|---|
| | Ingredients | Com. Ex. 10 | Com. Ex. 11 | Ex. 15 | Ex. 16 | Ex. 17 | Ex. 18 | Ex. 19 | Ex. 20 | Ex. 21 | Com. Ex. 12 |
| 1 | Water | 15 | 15 | 15 | 15 | 15 | 10 | 10 | 10 | 1 | 1 |
| 2 | Polyoxyethylene (20) glycerol triisostearate | — | 0.01 | 0.02 | 0.5 | — | — | — | — | — | — |
| 3 | Sorbitol monooleate | — | — | — | — | 0.5 | — | — | — | 0.1 | 2.5 |
| 4 | Monosodium N—lauroyl glutamate | — | — | — | — | — | 0.1 | — | — | — | — |
| 5 | Stearyltrimethyl ammonium chloride | — | — | — | — | — | — | 0.1 | — | — | — |
| 6 | Lauryl dimethyl aminoacetate betaine | — | — | — | — | — | — | — | 0.1 | — | — |
| 7 | Glycine | — | — | — | — | 0.5 | — | 0.5 | — | — | — |
| 8 | Glycerol | — | — | 0.5 | — | — | 1 | — | — | — | — |
| 9 | Nitrocellulose RS¼ (note 5) | 14 | 14 | 14 | 14 | 14 | 14 | 14 | 14 | 14 | 14 |
| 10 | Acrylic resin (note 11) | 12 | 12 | 12 | 12 | 12 | 12 | 12 | 12 | 12 | 12 |
| 11 | Acetyltributyl citrate | 5 | 5 | 5 | 5 | 5 | 5 | 5 | 5 | 5 | 5 |
| 12 | Camphor | 1.5 | 1.5 | 1.5 | 1.5 | 1.5 | 1.5 | 1.5 | 1.5 | 1.5 | 1.5 |
| 13 | n-Butyl acetate | 35.5 | 35.49 | 34.98 | 35 | 34.5 | 40.4 | 38.9 | 40.4 | 49.4 | 47.0 |
| 14 | Toluene | 15 | 15 | 15 | 15 | 15 | 15 | 15 | 15 | 15 | 15 |
| 15 | Pigment (note 13) | 1 | 1 | 1 | 1 | 1 | 1 | 1 | 1 | 1 | 1 |
| 16 | Organo-modified bentonite | 1 | 1 | 1 | 1 | 1 | 1 | 1 | 1 | 1 | 1 |

Note 13: Helindone pink/titanium dioxide (4/1)
Notes 5 and 11: Same as Tables 1 or 3

TABLE 6

| | Fingernail Cosmetic Compositions | | | | | | | | | |
|---|---|---|---|---|---|---|---|---|---|---|
| Testing Items | Com. Ex. 10 | Com. Ex. 11 | Ex. 15 | Ex. 16 | Ex. 17 | Ex. 18 | Ex. 19 | Ex. 20 | Ex. 21 | Com. Ex. 12 |
| Stability against separation | x | Δ | ○ | ⊚ | ⊚ | ⊚ | ⊚ | ⊚ | ⊚ | ⊚ |
| Stimulus upon application | | ⊚ | ⊚ | ⊚ | ⊚ | ⊚ | ⊚ | ⊚ | ⊚ | ⊚ |
| Ease of application | | ⊚ | ⊚ | ⊚ | ⊚ | ⊚ | ⊚ | ⊚ | ⊚ | ⊚ |
| Gloss of coating | | ⊚ | ⊚ | ⊚ | ⊚ | ⊚ | ⊚ | ⊚ | ⊚ | ⊚ |
| Peeling resistance (resistance to water) | | ⊚ | ⊚ | ⊚ | ⊚ | ⊚ | ⊚ | ⊚ | ⊚ | x |
| Safety (Split-nail) | — | ⊚ | ☆ | ⊚ | ⊚ | ⊚ | ☆ | ⊚ | ○ | ○ |
| Overall evaluation | x | Δ | ○ | ⊚ | ⊚ | ⊚ | ⊚ | ⊚ | ○ | x |

It is apparent from Table 6 that the fingernail cosmetic composition according to the present invention exhibits a good safety factor against damage to a fingernail and rarely causes split-nails due to a continuous application, and further, has a good stability against separation (emulsification), less stimulus (cold feeling) upon application, an ease of application, a glossy coating, and a good peeling resistance (resistance to water), and thus has satisfactory properties as a fingernail cosmetic composition.

EXAMPLES 22 to 26 and COMPARATIVE EXAMPLE 13

Six kinds of fingernail cosmetic compositions were prepared from the ingredients listed in Table 7.

Using the weight ratios shown in Table 7, acetyltriethyl citrate and n-butyl acetate were mixed with stirring. To the mixture, nitrocellulose, alkyd resin, sucrose benzoate and camphor were added and stirred until dissolved. Then, pigment and organo-modified bentonite were added and stirred until dispersed. To the dispersion, a mixture prepared by adding a moisturizing agent to an aqueous solution of hydroxypropylmethyl cellulose and mixing was added and stirred until emulsified. Thus, red-colored fingernail cosmetic compositions were formed.

These nail cosmetic compositions were tested as above-mentioned. The results are listed in Table 8.

sion, an amino acid was added and stirred until emulsified. Thus, red-colored fingernail cosmetic compositions were formed.

These nail cosmetic compositions were tested as above-mentioned. The results are listed in Table 10.

The tests and evaluations of the stability of the fragrance and color were carried out as follows:

Stability of Fragrance

The sample was charged in a glass bottle (15 ml) and left to stand at 50° C. for 2 months. After cooling to room temperature, the sample was applied on a fingernail and the degree of smell of acetic acid was determined. The evaluation was effected as follows:
◉ (good) . . . No smell of acetic acid
○ (acceptable) . . . Slight smell of acetic acid
Δ (bad) . . . Noticeable smell of acetic acid
x (unacceptable) . . . Strong smell of acetic acid

TABLE 7

(% by weight)

| Ingredients | Ex. 22 | Ex. 23 | Ex. 24 | Ex. 25 | Ex. 26 | Com. Ex. 13 |
|---|---|---|---|---|---|---|
| 1 Glycerol | — | 0.1 | 0.2 | — | — | — |
| 2 Propylene glycol | — | — | — | 2 | — | — |
| 3 Dipropylene glycol | — | — | — | — | 4 | 5 |
| 4 3% hydroxypropylmethyl cellulose aq. soln. (note 1) | 0.5 | 0.5 | 0.5 | 5 | 10 | 10 |
| 5 Nitrocellulose RS¼ (note 5) | 13 | 13 | 13 | 13 | 12 | 12 |
| 6 Alkyd resin (note 6) | 8 | 8 | 8 | 8 | 8 | 8 |
| 7 Sucrose benzoate | 4 | 4 | 4 | 4 | 4 | 4 |
| 8 Acetyltriethylcitrate | 5 | 5 | 5 | 5 | 5 | 5 |
| 9 Camphor | 1.5 | 1.5 | 1.5 | 1.5 | 1.5 | 1.5 |
| 10 n-Butyl acetate | 66 | 65.9 | 65.8 | 59.5 | 54.5 | 53.5 |
| 11 Pigment (note 7) | 1 | 1 | 1 | 1 | 1 | 1 |
| 12 Organo-bentonite gelling agent | 1 | 1 | 1 | 1 | 1 | 1 |

Notes 1, 5, 6 and 7: Same as Table 1.

TABLE 8

Fingernail Cosmetic Compositions

| Testing Items | Ex. 22 | Ex. 23 | Ex. 24 | Ex. 25 | Ex. 26 | Com. Ex. 13 |
|---|---|---|---|---|---|---|
| Stability against separation | ○ | ◉ | ◉ | ◉ | ◉ | ○ |
| Ease of application | ◉ | ◉ | ◉ | ◉ | ○ | ○ |
| Gloss of coating | ◉ | ◉ | ◉ | ◉ | ◉ | ◉ |
| Peeling resistance (Resistance to water) | ◉ | ◉ | ◉ | ◉ | ○ | Δ |
| Safety (Split-nail) | Δ | ○ | ◉ | ☆ | ☆ | — |

EXAMPLES 27 to 36 and COMPARATIVE EXAMPLES 14 to 16

Thirteen kinds of fingernail cosmetic compositions were prepared from the ingredients listed in Table 9.

Using the weight ratios shown in Table 9, acetyltributyl citrate and n-butyl acetate were mixed with stirring. To the mixture, nitrocellulose, alkyd resin, sucrose benzoate and camphor were added and stirred until dissolved. Then, pigment and organo-modified bentonite were added and stirred until dispersed. To the disper-

Stability of Color

The sample was charged in a glass bottle (15 ml) and left to stand at 50° C. for 2 months, and the degree of a color change was observed. The evaluation was effected as follows:
◉ (good) . . . No color change
○ (acceptable) . . . Slight color change
Δ (bad) . . . Noticeable color change
x (unacceptable) . . . Considerable color change.

TABLE 9

(% by weight)

| Ingredients | Ex. 27 | Com. Ex. 14 | Com. Ex. 15 | Ex. 28 | Ex. 29 | Ex. 30 | Ex. 31 | Ex. 32 | Ex. 33 | Ex. 34 | Ex. 35 | Ex. 36 | Com. Ex. 16 |
|---|---|---|---|---|---|---|---|---|---|---|---|---|---|
| 1 Aspartic acid | — | 0.5 | — | — | — | — | — | — | — | — | — | — | — |
| 2 Glutamic acid | — | — | 0.5 | — | — | — | 0.25 | — | — | — | — | — | — |
| 3 Arginine | — | — | — | 0.5 | — | — | — | — | — | — | — | — | — |
| 4 Histidine | — | — | — | — | 0.5 | — | 0.25 | — | — | — | — | — | — |
| 5 Glycine | — | — | — | — | — | 0.5 | — | — | — | — | — | — | — |

TABLE 9-continued

| | (% by weight) | | | | | | | | | | | | |
|---|---|---|---|---|---|---|---|---|---|---|---|---|---|
| Ingredients | Ex. 27 | Com. Ex. 14 | Com. Ex. 15 | Ex. 28 | Ex. 29 | Ex. 30 | Ex. 31 | Ex. 32 | Ex. 33 | Ex. 34 | Ex. 35 | Ex. 36 | Com. Ex. 16 |
| 6 Salt of arginine-aspartic acid | — | — | — | — | — | — | — | 0.5 | — | — | — | — | — |
| 7 Salt of lysine-glutamic acid | — | — | — | — | — | — | — | — | 0.03 | 0.05 | 1 | 3 | 4 |
| 8 3% hydroxypropylmethyl cellulose aq. soln. (note 1) | 10 | 10 | 10 | 10 | 10 | 10 | 10 | 10 | 5 | 5 | 10 | 15 | 15 |
| 9 Nitrocellulose RS¼ (note 5) | 13 | 13 | 13 | 13 | 13 | 13 | 13 | 13 | 13 | 13 | 13 | 13 | 13 |
| 10 Alkyd resin (note 6) | 8 | 8 | 8 | 8 | 8 | 8 | 8 | 8 | 8 | 8 | 8 | 8 | 8 |
| 11 Sucrose benzoate | 4 | 4 | 4 | 4 | 4 | 4 | 4 | 4 | 4 | 4 | 4 | 4 | 4 |
| 12 Acetyltriethyl citrate | 5 | 5 | 5 | 5 | 5 | 5 | 5 | 5 | 5 | 5 | 5 | 5 | 5 |
| 13 Camphor | 1.5 | 1.5 | 1.5 | 1.5 | 1.5 | 1.5 | 1.5 | 1.5 | 1.5 | 1.5 | 1.5 | 1.5 | 1.5 |
| 14 n-Butyl acetate | 56.5 | 56 | 56 | 56 | 56 | 56 | 56 | 56 | 61.47 | 61.45 | 55.5 | 48.8 | 47.8 |
| 15 Pigment (note 7) | 1 | 1 | 1 | 1 | 1 | 1 | 1 | 1 | 1 | 1 | 1 | 1 | 1 |
| 16 Organo-bentonite gelling agent | 1 | 1 | 1 | 1 | 1 | 1 | 1 | 1 | 1 | 1 | 1 | 0.7 | 0.7 |

Notes 1, 5, 6 and 7: Same a Table 1

TABLE 10

| | Fingernail Cosmetic Composition | | | | | | | | | | | | |
|---|---|---|---|---|---|---|---|---|---|---|---|---|---|
| Testing Items | Ex. 27 | Com. Ex. 14 | Com. Ex. 15 | Ex. 28 | Ex. 29 | Ex. 30 | Ex. 31 | Ex. 32 | Ex. 33 | Ex. 34 | Ex. 35 | Ex. 36 | Com. Ex. 16 |
| Stability of fragrance | x | x | x | ◉ | ◉ | ○ | ○ | ○ | △ | ○ | ◉ | ◉ | ◉ |
| Stability of color | ◉ | ◉ | ◉ | ○ | ◉ | ◉ | ◉ | ◉ | ◉ | ◉ | ◉ | ○ | ○ |
| Ease of application | ◉ | ◉ | ◉ | ◉ | ◉ | ◉ | ◉ | ◉ | ◉ | ◉ | ◉ | ◉ | ◉ |
| Gloss of coating | ◉ | ◉ | ◉ | ◉ | ◉ | ○ | ◉ | ○ | ◉ | ◉ | ◉ | ○ | ○ |
| Peeling resistance (resistance to water) | ◉ | ◉ | ◉ | ◉ | ◉ | ◉ | ◉ | ◉ | ◉ | ◉ | ◉ | ○ | △ |

It is apparent from Table 10 that the fingernail cosmetic composition containing a fragrance-maintaining agent according to the present invention exhibits a good factor against damage to a safety fingernail, and an excellent stability of fragrance and color.

The compositions of Comparative Examples 14 and 15 contain acidic amino acid, and thus do not have a good stability of fragrance. The composition of Comparative Example 16 has an excess amount of the salt of amino acids, and thus does not show a good peeling resistnace (resistance to water).

We claim:

1. A fingernail cosmetic composition containing at least one resin, at least one organic solvent, 0.5 to 30% of water based on the total weight of the composition, and a water-incorporating compound having at least one hydrophilic moiety and at least one lipophilic moiety, the weight ratio of the water-incorporating compound to water ranging from 0.1 to 200:100, said water-incorporating compound being at least one member selected from the group consisting of water-soluble polymers having an average molecular weight of 1,000 to 2,000,000 and oil-soluble polymers having an average molecular weight of 1,000 to 2,000,000.

2. A composition according to claim 1, wherein the water-incorporating compound is an oil-soluble polymer having an average molecular weight of 1,000 to 1,000,000.

3. A composition according to claim 1, wherein the water-incorporating compound is a surface-active agent.

4. A composition according to claim 1, further comprising a moisturizing agent selected from the group consisting of a polyol, sodium lactate, sodium pyrrolidone carboxylate, a glycerol ethylene oxide adduct and mixtures thereof, the amount of the moisturizing agent incorporated being 0.1 to 4% by weight with respect to the total weight of the composition.

5. A composition according to claim 1, further comprising, as a fragrance-maintaining agent, a compound capable of controlling hydrolysis of an ester solvent at an elevated temperature, the amount of the fragrance-maintaining agent incorporated being 0.05 to 3% by weight relative to the total weight of the composition.

6. A composition according to claim 5, wherein the fragrance-maintaining agent is a neutral or basic amino acid, or a salt of an acidic amino acid and a basic amino acid.

* * * * *